US012797251B2

(12) United States Patent
Kharkar et al.

(10) Patent No.: US 12,797,251 B2
(45) Date of Patent: Nov. 17, 2026

(54) DRESSING EMPLOYING FEATURES FOR PROTECTION AGAINST MACERATION

(71) Applicant: Solventum Intellectual Properties Company, Maplewood, MN (US)

(72) Inventors: Prathamesh Madhav Kharkar, San Antonio, TX (US); Diwi L. Allen, San Antonio, TX (US); Marisa Schmidt, San Antonio, TX (US); Christopher Allen Carroll, San Antonio, TX (US)

(73) Assignee: Solventum Intellectual Properties Company, Eagan, MN (US)

( * ) Notice: Subject to any disclaimer, the term of this patent is extended or adjusted under 35 U.S.C. 154(b) by 1125 days.

(21) Appl. No.: 17/621,157

(22) PCT Filed: May 19, 2020

(86) PCT No.: PCT/US2020/033626
§ 371 (c)(1),
(2) Date: Dec. 20, 2021

(87) PCT Pub. No.: WO2020/263457
PCT Pub. Date: Dec. 30, 2020

(65) Prior Publication Data

US 2022/0354701 A1 Nov. 10, 2022

Related U.S. Application Data

(60) Provisional application No. 62/867,001, filed on Jun. 26, 2019.

(51) Int. Cl.
*A61F 13/00* (2024.01)
*A61F 13/0203* (2024.01)
(Continued)

(52) U.S. Cl.
CPC .... *A61F 13/00063* (2013.01); *A61F 13/0206* (2013.01); *A61F 13/0213* (2013.01);
(Continued)

(58) Field of Classification Search
CPC .. A61F 13/05; A61F 13/0206; A61F 13/0213; A61F 13/0256; A61F 13/00063;
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

International Search Report and Written Opinion for Corresponding Application No. PCT/US2020/033626 mailed Oct. 26, 2020.
(Continued)

*Primary Examiner* — Rebecca E Eisenberg
*Assistant Examiner* — Timothy L Flynn

(57) ABSTRACT

Dressings for treating a tissue site with negative pressure are disclosed, which may include a dressing having multiple layers and incorporating a material adapted to neutralize proteolytic enzymes. In one example embodiment, a dressing may include a first layer comprising a hydrophobic gel having a plurality of apertures. A material adapted to neutralize proteolytic enzymes may be applied to a surface of the first layer. The dressing may further include a second layer comprising a fenestrated film and coupled to the first layer. Additionally, the dressing may include a third layer comprising a manifold, which in some instances may be a
(Continued)

polymeric foam. The dressing may further include a fourth layer comprising a polymer drape.

16 Claims, 5 Drawing Sheets

(51) Int. Cl.
*A61F 13/0206* (2024.01)
*A61F 13/0246* (2024.01)
*A61F 13/05* (2024.01)
*A61M 1/00* (2006.01)

(52) U.S. Cl.
CPC .......... *A61F 13/0253* (2013.01); *A61F 13/05* (2024.01); *A61M 1/915* (2021.05)

(58) Field of Classification Search
CPC .......... A61F 13/00051; A61F 13/01008; A61F 13/01017; A61F 13/01029; A61M 1/915; A61L 15/28; A61L 15/44; A61L 15/325; A61L 2300/434
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2004/0030304 | A1* | 2/2004 | Hunt ................. A61F 13/01042 604/317 |
| 2009/0227969 | A1* | 9/2009 | Jaeb .................. A61F 13/00063 604/313 |
| 2011/0251566 | A1* | 10/2011 | Zimnitsky ............... A61P 29/00 604/289 |
| 2014/0163447 | A1* | 6/2014 | Wieland ................ A61L 15/225 264/28 |

(56) References Cited

U.S. PATENT DOCUMENTS

| | | | | |
|---|---|---|---|---|
| 2014/0163491 | A1 | 6/2014 | Schuessler et al. | |
| 2014/0276493 | A1 | 9/2014 | Leung et al. | |
| 2015/0080788 | A1 | 3/2015 | Blott et al. | |
| 2016/0030646 | A1* | 2/2016 | Hartwell | A61F 13/05 604/319 |
| 2016/0038626 | A1* | 2/2016 | Locke | A61L 15/42 514/772.3 |
| 2018/0028713 | A1* | 2/2018 | Agarwal | A61L 15/44 |
| 2018/0353341 | A1* | 12/2018 | Locke | A61F 13/0223 |
| 2018/0353342 | A1 | 12/2018 | Locke et al. | |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2011008497 | A2 | 1/2011 |
| WO | 2011127188 | A2 | 10/2011 |
| WO | 2016025293 | A1 | 2/2016 |
| WO | 2018226624 | A1 | 12/2018 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc, Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc, King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

1 Japanese Notice of Rejection for corresponding application 2021-575353, dated Oct. 29, 2024.

Japanese Notice of Rejection for corresponding application 2021-575353, dated Apr. 2, 2024.

Japanese Notice of Rejection for corresponding application 2025-077104, dated Jun. 2, 2026.

* cited by examiner

DRESSING EMPLOYING FEATURES FOR PROTECTION AGAINST MACERATION

RELATED APPLICATIONS

The present application claims priority to U.S. Provisional Patent Application No. 62/867,001, entitled "Dressing Employing Features for Protection Against Maceration," filed Jun. 26, 2019, which is incorporated herein by reference for all purposes.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

Dressings and systems for treating a tissue site may incorporate one or more means for inhibiting excessive activity of proteolytic enzymes in wound fluids. For example, the tissue dressings may comprise sacrificial proteolytic enzyme substrates for reducing or preventing such proteolytic enzymes from degrading new tissue as it forms as part of a healing wound. Normal endogenous levels of wound proteases are important for tissue remodeling during the healing process. For example, matrix metalloproteases (MMPs) are among the proteases typically present in wounds and can play an important role in the wound healing response. However, in excess, or when remaining in contact with healing areas of a wound site, such as wound margins, or peri-wound, such enzymes may continually break down the new tissue that is being formed. Prolonged contact of wound fluids, particularly when there may be elevated levels of proteolytic enzymes present, may also lead to maceration of the wound margins, or peri-wound areas. Specifically, the presence of water in the peri-wound areas may result in hydration of the stratum corneum, which may reduce the barrier function of typical healthy skin. Various proteolytic enzymes present in the wound exudate may then subsequently penetrate the healthy skin, resulting in maceration. These factors may also contribute to the wound not healing quickly or becoming stalled.

Accordingly, in certain aspects, dressings incorporating one or more substrates for preventing detrimental or undesirable effects of wound fluids and associated proteolytic enzymes on healthy or healing skin are disclosed. Such substrates, for example one or more biopolymers, may function as sacrificial substrates for enzyme modulation or neutralization, may function as enzyme deactivators, and/or may serve as enzyme sequestrators in order to reduce levels of proteolytic enzymes that may otherwise have a negative effect on wound healing. One or more substrates for MMPs as well as for other proteolytic enzymes, may be included. For example, possible MMP substrates include, but are not limited to, collagen, gelatin, elastin, casein, albumin, fibrinogen, fibronectin, and combinations and hydrolysates thereof. In some embodiments, it may be particularly advantageous to include a sacrificial substrate comprising collagen, which may be a suitable substrate for many of the MMPs that are most prevalent in wounds. In some instances, proteins for use as sacrificial substrates may be hydrolyzed or partially hydrolyzed by treatment with a strong acid or base. Such treatment can fragment the subject proteins and generate a more accessible peptide sequence to bind to proteolytic enzymes. As described below in the disclosed example embodiments, the sacrificial proteolytic substrates may be integrated with tissue dressings and systems for use with negative-pressure wound therapy.

For example, in some embodiments, a dressing for treating a tissue site may comprise a first layer, a second layer adjacent to the first layer, a third layer adjacent to the first layer opposite the second layer, a fourth layer adjacent to the third layer opposite the first layer, and a fifth layer adjacent to the fourth layer opposite the third layer. The first layer may comprise a hydrophobic gel having a plurality of apertures. The second layer may comprise a material adapted to neutralize proteolytic enzymes. The third layer may comprise a polymer film having a plurality of fluid restrictions that are configured to expand in response to a pressure gradient. The fourth layer may comprise a manifold. The fifth layer may comprise a polymer drape. In some embodiments, the material adapted to neutralize proteolytic enzymes of the second layer may include a sacrificial substrate. In some additional embodiments, the dressing may be fluidly coupled to a negative-pressure source as part of a system for treating a tissue site.

In some additional embodiments, a dressing for treating a tissue site with negative pressure may comprise a first film, a second film coupled to the first film, a third film adjacent to the first film opposite the second film, and a manifold layer adjacent to the third film. The first film may comprise a perforated silicone gel coating. The second film may comprise an enzyme-modulating material. The third film may comprise a non-porous material and a plurality of fenestrations. The manifold layer may comprise foam.

In further embodiments, a dressing for treating a tissue site with negative pressure may comprise a first layer, a second layer, and a third layer adapted to be positioned adjacent to the first layer opposite the second layer. The first layer may comprise a hydrophobic gel having a plurality of apertures, and the second layer may comprise a material adapted to neutralize proteolytic enzymes and may have a plurality of fenestrations. The third layer may comprise a polymer drape.

In yet some additional embodiments, a dressing for treating a tissue site with negative pressure may comprise a first layer, a second layer adapted to be coupled to the first layer, a third layer adapted to be positioned adjacent to the second layer opposite the first layer, a fourth layer adapted to be positioned adjacent the third layer opposite the second layer, and a fifth layer adapted to be coupled to the fourth layer opposite the third layer. The first layer may include a hydrophobic gel having a plurality of apertures, the second layer may comprise a polymer film having a plurality of fenestrations, and the third layer may comprise a manifold. The fourth layer may have a plurality of openings and may comprise a material adapted to neutralize proteolytic enzymes. The fifth layer may comprise a polymer drape.

In some further embodiments, a dressing for treating a tissue site may comprise a first layer, a second layer, and a third layer adapted to be disposed between the first layer and the second layer. The first layer may have a plurality of apertures and may comprise a hydrophobic gel adhesive and a material adapted to neutralize proteolytic enzymes. The second layer may comprise a manifold, and the third layer may comprise a polymer film having a plurality of fenestrations. The dressing may further include a fourth layer adapted to be coupled to the second layer opposite the third layer, and the fourth layer may comprise a polymer drape.

In some additional embodiments, a dressing for treating a tissue site may comprise a hydrophobic gel layer, an enzyme-modulating layer adjacent to the hydrophobic gel layer, a fluid control layer adjacent to the hydrophobic gel layer opposite the enzyme-modulating layer, and a manifold layer adjacent the fluid control layer opposite the hydrophobic gel layer. The manifold layer may comprise a foam.

In still some additional embodiments, a dressing for treating a tissue site with negative pressure may comprise a perforated silicone gel, a first film comprising apertures and an enzyme-modulating material, a second film comprising a plurality of fenestrations, a manifold, and a cover. The perforated silicone gel, the first film, the second film, the manifold, and the cover may be assembled in a stacked relationship with the perforated silicone gel and the cover enclosing the second film and the manifold. The first film may be configured to contact the tissue site.

In yet further embodiments, a dressing for treating a tissue site with negative pressure may comprise a first layer comprising an enzyme-modulating material, a second layer adapted to be coupled to the first layer, a third layer adapted to be coupled to the second layer opposite the first layer, and a fourth layer adapted to be positioned adjacent to the third layer opposite the second layer. The second layer may include a hydrophobic gel. The third layer may be in the form of a fenestrated film, and the fourth layer may comprise a manifold. The first layer may be in the form of a ring having an outer structural portion and an opening, wherein the ring is adapted to be applied to a first surface of the second layer. Additionally, the dressing may further include a fifth layer adapted to be coupled to the fourth layer opposite the third layer, and the fifth layer may comprise a polymer drape. In some additional embodiments, the first layer may be applied as a pattern coating to a first surface of the second layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
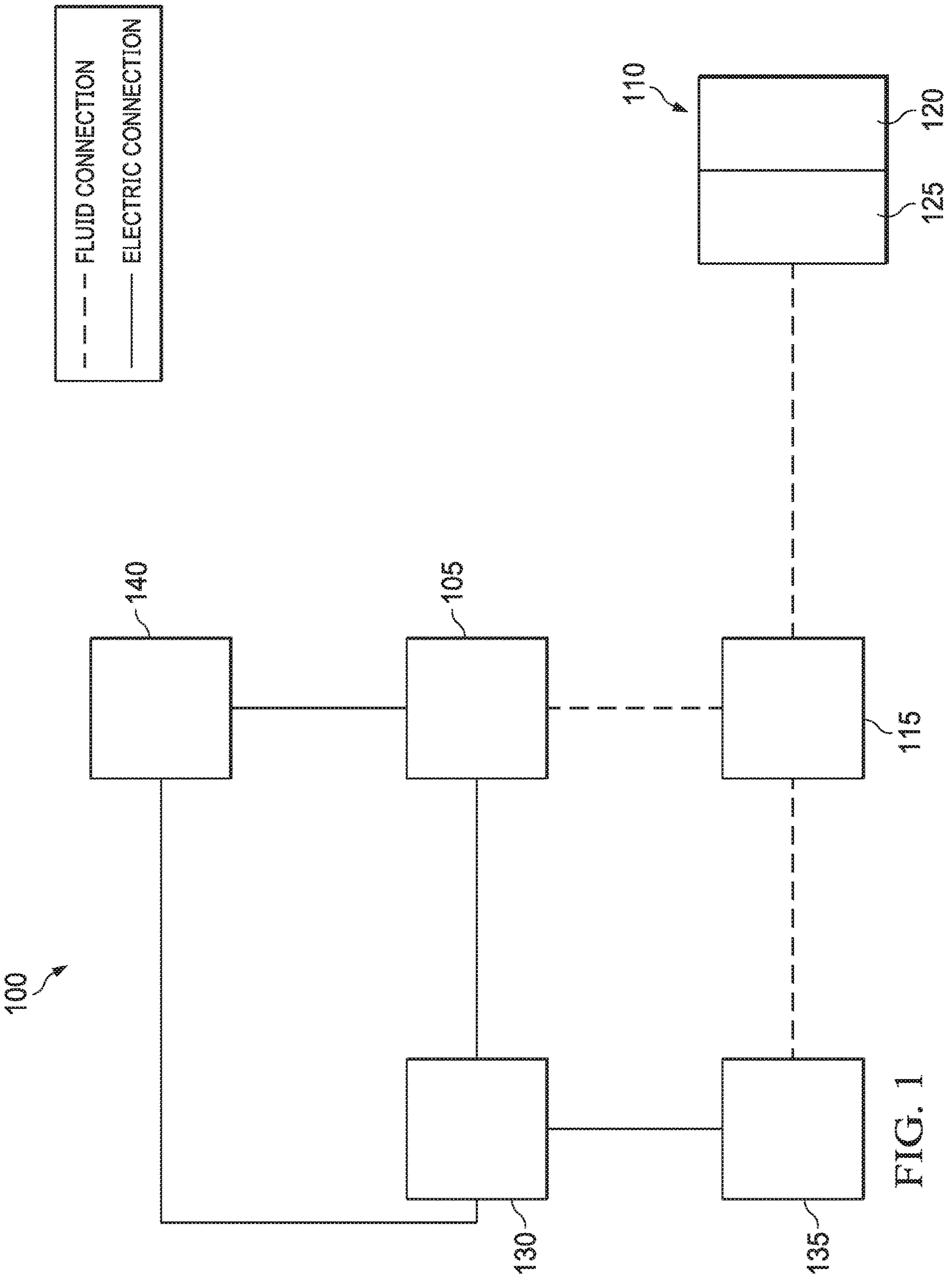
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minn.; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2:
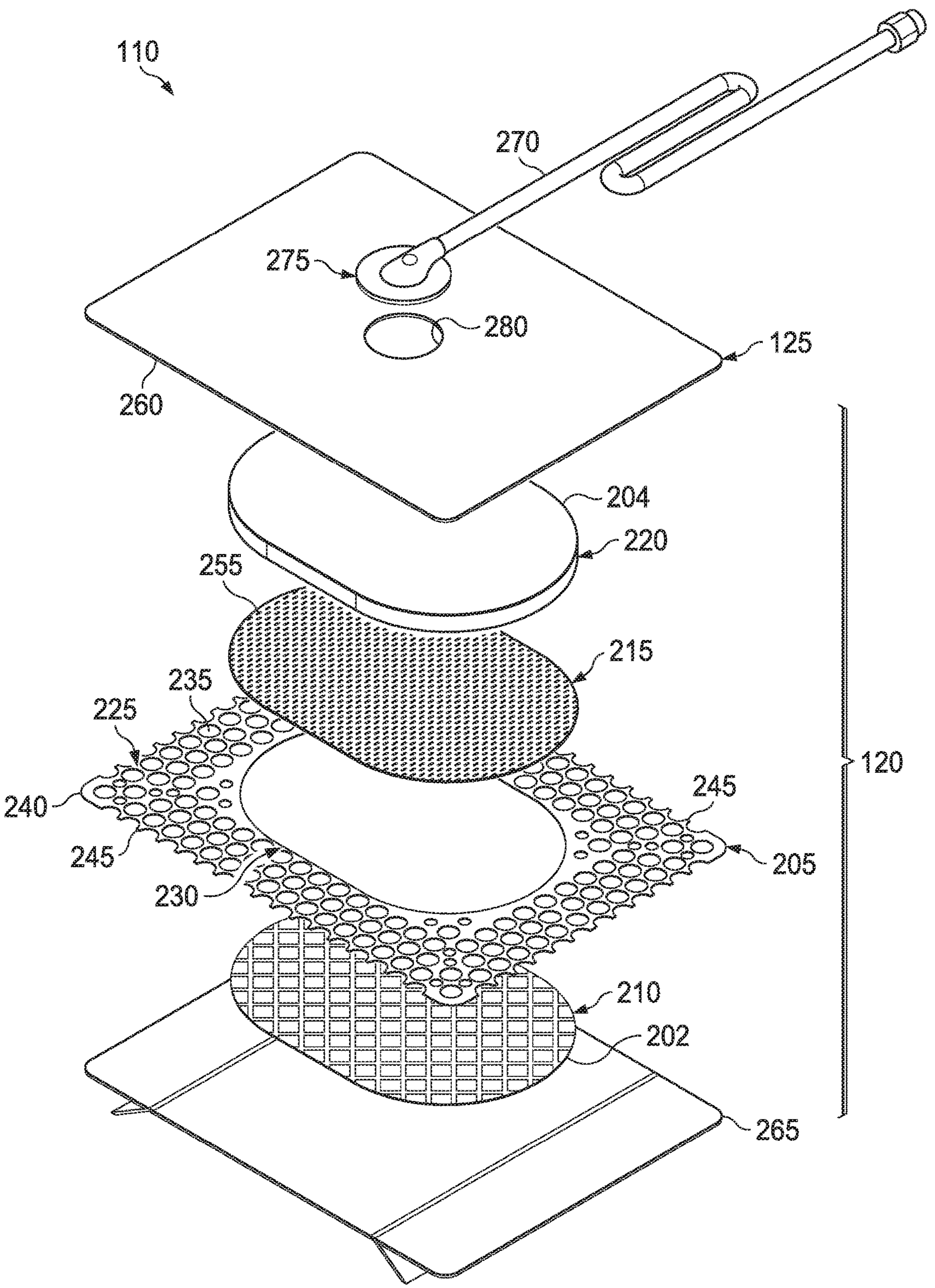
FIG. 2 is an assembly view of an example of a dressing illustrating additional details that may be associated with some example embodiments of the therapy system of FIG. 1.

FIG. 2 is an assembly view of an example of the dressing 110 of FIG. 1, illustrating additional details that may be associated with some embodiments in which the tissue interface 120 comprises more than one layer. The tissue interface 120 may have a first side 202 and a second side 204. In the example of FIG. 2, the tissue interface 120 comprises a first layer 205, a second layer 210, a third layer 215, and a fourth layer 220. The first layer 205, the second layer 210, the third layer 215, and the fourth layer 220 may be stacked in a variety of configurations. For example, the third layer 215 may be disposed between the first layer 205 and the fourth layer 220. In some embodiments, second layer 210 may be disposed adjacent to the first layer 205. For example, the second layer 210 may be disposed adjacent to the first layer 205 opposite the third layer 215. In other examples, the second layer 210 may be disposed between the first layer 205 and the third layer 215. Additionally, the fourth layer 220 may be disposed adjacent to the third layer 215 opposite the first layer 205. For example, the first layer 205, the second layer 210, the third layer 215, and the fourth layer 220 may be stacked so that the first layer 205 is in contact with the second layer 210 and the third layer 215, is in contact with the first layer 205 and the fourth layer 220. One or more of the first layer 205, the second layer 210, the third layer 215, and the fourth layer 220 may also be bonded to an adjacent layer in some embodiments, however in some instances, one or more layers of the tissue interface 120, such as for example the fourth layer 220, may be freely placed or positioned between the other layers of the dressing 110 without being bonded or attached to the adjacent layers. The overall dressing 110, including the individual layers of the tissue interface 120, may be any number of different shapes, based on the particular anatomical needs of a tissue site. For example, the dressing 110 and included layers of the tissue interface 120 may have a square, rectangular, oval, circular, hexagonal, or other shape.

The first layer 205 may be a sealing layer comprising or consisting essentially of a soft, pliable material suitable for providing a fluid seal with a tissue site, and may have a substantially flat surface. For example, the first layer 205 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the first layer 205 may have a thickness between about 200 microns (μm) and about 1000 microns (μm). In some embodiments, the first layer 205 may have a hardness between about 5 Shore 00 and about 80 Shore 00. Further, the first layer 205 may be comprised of hydrophobic or hydrophilic materials. The first layer 205 may be adjusted in thickness and/or in tackiness depending on the overall arrangement and positioning of other layers in the tissue interface 120. For example, the first layer 205 may comprise a silicone gel with a tackiness that may be adjusted by increasing or decreasing the tackifier concentration of the silicone gel. In some embodiments, the thickness of a silicone gel of the first layer 205 may be increased to increase the overall adherence of the tissue interface 120 to a tissue site.

In some embodiments, the first layer 205 may be a hydrophobic-coated material. For example, the first layer 205 may be formed by coating a spaced material, such as, for example, woven, nonwoven, molded, or extruded mesh with a hydrophobic material. The hydrophobic material for the coating may be a soft silicone for example.

The first layer 205 may have a peripheral area, such as a periphery 225, surrounding or around an interior portion having at least one treatment aperture 230. The first layer 205 may have apertures 235 disposed through the periphery 225. The first layer 205 may also have corners 240 and edges 245. The corners 240 and the edges 245 may be part of the periphery 225. In some examples, as illustrated in FIG. 2, the treatment aperture 230 may be symmetrical and centrally disposed in the first layer 205. The treatment aperture 230 may approximately correspond to a surface area of the fourth layer 220 in some examples. For example, the treatment aperture 230 may form a frame, window, or other opening around a surface of the fourth layer 220. The treatment aperture 230 may allow communication of negative pressure and wound fluids between the second layer 210 and the third layer 215.

The apertures 235 may be formed by cutting or by application of local radio-frequency (RF) or ultrasonic energy, for example, or by other suitable techniques for forming an opening. The apertures 235 may have a uniform distribution pattern, or may be randomly distributed on the first layer 205. The apertures 235 in the first layer 205 may have many shapes, including circles, squares, stars, ovals, polygons, slits, complex curves, rectilinear shapes, triangles, for example, or may have some combination of such shapes. Each of the apertures 235 may have uniform or similar geometric properties. For example, in some embodiments, each of the apertures 235 may be circular apertures, having substantially the same diameter. In some embodiments, the diameter of each of the apertures 235 may be between about 1 millimeter and about 50 millimeters. In other embodiments, the diameter of each of the apertures 235 may be between about 1 millimeter and about 20 millimeters.

In other embodiments, geometric properties of the apertures 235 may vary. For example, the diameter of the apertures 235 may vary depending on the position of the apertures 235 in the first layer 205, as illustrated in FIG. 2. For example, in some embodiments, the apertures 235 disposed in the periphery 225 may have a diameter between about 9.8 millimeters to about 10.2 millimeters. In some embodiments, the apertures 235 disposed in the corners 240 may have a diameter between about 7.75 millimeters to about 8.75 millimeters.

At least one of the apertures 235 in the periphery 225 of the first layer 205 may be positioned at the edges 245 of the periphery 225, and may have an interior cut open or exposed at the edges 245 that is in fluid communication in a lateral direction with the edges 245. The lateral direction may refer to a direction toward the edges 245 and in the same plane as the first layer 205. As shown in the example of FIG. 2, the apertures 235 in the periphery 225 may be positioned proximate to or at the edges 245 and in fluid communication in a lateral direction with the edges 245. The apertures 235 positioned proximate to or at the edges 245 may be spaced substantially equidistant around the periphery 225 as shown in the example of FIG. 2. Alternatively, the spacing of the apertures 235 proximate to or at the edges 245 may be irregular.

The second layer 210 may comprise or consist essentially of a material suited for modulating or neutralizing enzymes at a tissue site. The target enzymes, such as proteolytic enzymes, are enzymes that could potentially lead to maceration at or around the tissue site if allowed to accumulate in excess or remain in prolonged contact with the tissue site. The second layer 210 may provide the tissue interface 120 with a means for neutralizing proteolytic enzymes to prevent possible maceration at the tissue site. In particular, the second layer 210 may reduce or prevent the risk of maceration should a peri-wound area of the tissue site become exposed to wound exudates containing the proteolytic enzymes.

The second layer 210 may comprise a variety of materials that may be suited for neutralizing proteolytic enzymes. In some instances, the second layer 210 may comprise one or more materials that may serve as a sacrificial substrate, an enzyme deactivator, an enzyme sequestrator, or a combination of such functions. In some embodiments, the second layer 210 may comprise a biologically-derived polymer including collagen, gelatin, collagen-like proteins, collagen-like peptides, or any combination of these materials. Sacrificial substrates of the second layer 210 may also include hyaluronic acid, chondroitin sulfate, collagen-mimic peptides, among others. Additionally, the second layer 210 may additionally or alternatively comprise cellulose or a cellulose derivative, such as oxidized regenerated cellulose (ORC), or chemically-modified cellulose. In some embodiments, the second layer 210 may comprise an enzyme sequestrator or deactivator, in the form of a binding decoy molecule or metal-ion chelating agents. Example chelating agents may include ethylenediaminetetraacetic acid (EDTA) and ethylene glycol tetraacetic acid (EGTA), among others. Enzyme deactivators may also include MMP inhibitors, such as tissue inhibitors of metalloproteinases (TIMPs), or small molecule protease inhibitors, such as thrombospondin-1, thrombospondin-2, elastase inhibitor 2, alpha 1 antitrypsin, pepstatin A, aprotinin, and leupeptin. Metalloprotein inhibitors with zinc-binding groups or copper analogs may also be useful in binding harmful metalloproteases or activating beneficial metalloproteases, and thus may also serve as enzyme sequestrators.

The second layer 210 may include a variety of different combinations or mixtures of materials suitable for neutralizing proteolytic enzymes. For example, some embodiments of the second layer 210 may comprise a combination of gelatin and collagen. Some additional embodiments of the second layer 210 may comprise a combination of collagen and ORC materials. For example, the second layer 210 may comprise a composite of approximately 50% collagen and 50% ORC, and in some preferred embodiments, the second layer 210 may comprise a composite of approximately 55% collagen and 45% ORC by weight. However, the proportions of each of the collagen and ORC may vary. For example, the second layer 210 may comprise a composite of collagen and ORC, with the amount of collagen ranging from 20% to 80% of the total weight of the second layer 210 and the amount of ORC ranging from 20% to 80% of the total weight of the second layer 210. In some embodiments, the second layer 210 may comprise or consist essentially of material found in PROMOGRAN™ Matrix Wound Dressing, commercially available from Kinetic Concepts, Inc. of San Antonio, Texas.

The arrangement of the second layer 210 may vary depending on the particular application of the tissue interface 120. For example, the second layer 210 may be substantially in the form of a sheet forming a portion of the first side 202 of the tissue interface 120. In some illustrative embodiments, as depicted in FIG. 2, the second layer 210 may be sized so as to be positioned under the treatment aperture 230, such as to cover the treatment aperture 230, as well as some of the periphery 225 of the first layer 205 on the first side 202 of the tissue interface 120. As illustrated in FIG. 2, the second layer 210 may have substantially an oval shape that may generally correspond to the shape of the treatment aperture 230 of the first layer 205. In some instances, the second layer 210 may comprise a grid-like structure, so that there is a presence of enzyme-neutralizing material positioned across a significant portion of the first side 202 of the tissue interface 120, while also allowing for a substantial open area, in the form of apertures or pores, of the second layer 210 so as to allow sufficient communication of negative pressure and/or other gasses and fluids between the tissue site and other layers of the dressing 110. The grid-like structure of the second layer 210 may comprise a plurality of segments of enzyme-neutralizing material arranged to form the structure of the second layer 210, with a plurality of apertures positioned among the plurality of segments of enzyme-neutralizing material. For example, the grid-like structure of the second layer 210 may comprise a first plurality of segments of enzyme-neutralizing material and a second plurality of segments of enzyme-neutralizing material. In some embodiments, each segment of the first plurality of segments of enzyme-neutralizing material may be arranged substantially parallel to the other segments of the first plurality of segments of enzyme-neutralizing material, and each segment of the second plurality of segments of enzyme-neutralizing material may be arranged substantially parallel to the other segments of the second plurality of segments of enzyme-neutralizing material. At least one of the first plurality of segments of enzyme-neutralizing material may intersect with one or more of the second plurality of segments of enzyme-neutralizing material. For example, the first plurality of segments of enzyme-neutralizing material may be arranged substantially perpendicular to the second plurality of segments of enzyme-neutralizing material.

As also illustrated in FIG. 2, the second layer 210 may not cover or overlap with a significant outer portion of the periphery 225 of the first layer 205, which therefore may allow for an adhesive material positioned on an underside of the cover 125, such as adhesive 260 shown in FIG. 2, to pass through at least a portion of the apertures 235 in the periphery 225 of the first layer 205 and make contact and form a seal with an area of tissue, such as epidermis, around the tissue site. In some examples, the second layer 210 may obstruct some portions of some of the apertures 235, which can prevent some adhesive 260 from being in direct contact with the tissue site. The apertures 235 may be configured to allow a sufficient amount of the adhesive 260 to pass through the apertures 235 in the periphery 225 to form a sufficient seal with an attachment surface surrounding the tissue site.

The second layer 210 may also be present in a variety of other structural and material configurations. For example, the second layer 210 may have a different shape, such as a square, circular, or rectangular shape. Moreover, regardless of shape, the second layer 210 may either be in the form of a solid sheet or may be more like a grid-like structure having openings or apertures in the material of the second layer 210. In some embodiments, each of the openings may have a diameter of between 1 mm and 10 mm. In some other instances, each of the openings may be in the form of a slot having a length between 1 mm and 10 mm and a width between 1 mm and 5 mm. For example, each of the openings may have a polygonal shape or square shape having sides with a length of between 1 mm and 10 mm. In some additional or alternative embodiments, the second layer 210 may comprise one or more enzyme-neutralizing materials dispersed in a pattern, or in one or more segments, across the second layer 210. For example, one portion of the second layer 210 may comprise collagen, while another portion of the second layer 210 may comprise oxidized regenerated cellulose (ORC). In another example, substantially the entire second layer 210 may comprise a mixture of collagen and ORC, with one section of the second layer 210 having a greater proportional amount of collagen and another section of the second layer 210 having a greater proportional amount of ORC. In some additional embodiments, the second layer 210 may include a blend of collagen and gelatin, which may offer some cost-savings benefits.

The second layer 210 may range in size and associated dimensions, depending on the particular configuration of the tissue interface 120 and/or the dressing 110. In some embodiments, the second layer 210 may have a thickness between approximately 5 micrometers and 5000 micrometers. In some particular embodiments, the second layer 210 may have a thickness in a range of 50 micrometers to 100 micrometers. Additionally, the second layer 210 may be perforated or fenestrated to allow air to flow through the second layer 210 for effective communication of negative pressure within the tissue interface 120.

The second layer 210 may also assist with reducing or preventing the presence of deleterious or infectious substances within the tissue interface 120 and at the tissue site. For example, the material of the second layer 210 may trap and/or treat bacteria or other microbial agents that may be present in wound fluids and pose a risk to the tissue site. The second layer 210 may therefore provide an antimicrobial benefit to the tissue interface 120.

The third layer 215 may comprise or consist essentially of a means for controlling or managing fluid flow. In some embodiments, the third layer 215 may comprise or consist essentially of a liquid-impermeable, elastomeric material. For example, the third layer 215 may comprise or consist essentially of a polymer film. The third layer 215 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the third layer 215 may have a substantially flat surface, with height variations limited to 0.2 millimeters over a centimeter.

In some embodiments, the third layer 215 may be hydrophobic. The hydrophobicity of the third layer 215 may vary, but may have a contact angle with water of at least ninety degrees in some embodiments. In some embodiments the third layer 215 may have a contact angle with water of no more than 150 degrees. For example, in some embodiments, the contact angle of the third layer 215 may be in a range of at least 90 degrees to about 120 degrees, or in a range of at least 120 degrees to 150 degrees. Water contact angles can be measured using any standard apparatus. The hydrophobicity of the third layer 215 may be further enhanced with a hydrophobic coating of other materials, such as silicones and fluorocarbons, either as coated from a liquid, or plasma coated. In some embodiments, for example, the third layer 215 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed.

The third layer 215 may also be suitable for welding to other layers, including the fourth layer 220. For example, the third layer 215 may be adapted for welding to polyurethane foams using heat, RF welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. For example, more polar films suitable for laminating to a polyethylene film include polyamide, co-polyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

The area density of the third layer 215 may vary according to a prescribed therapy or application. In some embodiments, an area density of less than 40 grams per square meter may be suitable, and an area density of about 20-30 grams per square meter may be particularly advantageous for some applications.

As illustrated in the example of FIG. 2, the third layer 215 may have one or more fluid restrictions 255, which can be distributed uniformly or randomly across the third layer 215. The fluid restrictions 255 may be bi-directional and pressure-responsive. For example, the fluid restrictions 255 can generally comprise or consist essentially of an elastic passage that is normally unstrained to substantially reduce liquid flow, and can expand in response to a pressure gradient. In some embodiments, the fluid restrictions 255 may comprise or consist essentially of perforations in the third layer 215. Perforations may be formed by removing material from the third layer 215. For example, perforations may be formed by cutting through the third layer 215, which may also deform the edges of the perforations in some embodiments. In the absence of a pressure gradient across the perforations, the passages may be sufficiently small to form a seal or flow restriction, which can substantially reduce or prevent liquid flow. Additionally or alternatively, one or more of the fluid restrictions 255 may be an elastomeric valve that is normally closed when unstrained to substantially prevent liquid flow, and can open in response to a pressure gradient. A fenestration in the third layer 215 may be a suitable valve for some applications. Fenestrations may also be formed by removing material from the third layer 215, but the amount of material removed and the resulting dimensions of the fenestrations may be an order of magnitude less than perforations, and may not deform the edges.

For example, some embodiments of the fluid restrictions 255 may comprise or consist essentially of one or more slots or combinations of slots in the third layer 215. In some examples, the fluid restrictions 255 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeter may be particularly suitable for many applications. A tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

As illustrated in the example of FIG. 2, the fourth layer 220 may form the second side 204 of the tissue interface 120. The fourth layer 220 may comprise or consist essentially of a manifold or manifold layer, which provides a means for collecting or distributing fluid across the tissue interface 120 under pressure. For example, the fourth layer 220 may be adapted to receive negative pressure from a source and distribute negative pressure through multiple apertures across the tissue interface 120, which may have the effect of collecting fluid from across a tissue site and drawing the fluid toward the source of negative pressure.

In some illustrative embodiments, the fourth layer 220 may comprise a plurality of pathways, which can be interconnected to improve distribution or collection of fluids. In some embodiments, the fourth layer 220 may comprise or consist essentially of a porous material having interconnected fluid pathways. For example, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the fourth layer 220 may additionally or alternatively comprise projections that form interconnected fluid pathways. For example, the fourth layer 220 may be molded to provide surface projections that define interconnected fluid pathways. Any or all of the surfaces of the fourth layer 220 may have an uneven, coarse, or jagged profile In some embodiments, the fourth layer 220 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the fourth layer 220 may also vary according to needs of a prescribed therapy. For example, the tensile strength of a foam may be increased for instillation of topical treatment solutions. The 25% compression load deflection of the fourth layer 220 may be at least 0.35 pounds per square inch, and the 65% compression load deflection may be at least 0.43 pounds per square inch. In some embodiments, the tensile strength of the fourth layer 220 may be at least 10 pounds per square inch. The fourth layer 220 may have a tear strength of at least 2.5 pounds per inch. In some embodiments, the fourth layer 220 may be a foam comprised of polyols such as polyester or polyether, isocyanate such as toluene diisocyanate, and polymerization modifiers such as amines and tin compounds. In one non-limiting example, the fourth layer 220 may be a reticulated polyurethane ether foam such as used in GRANUFOAM™ dressing or V.A.C. VERAFLO™ dressing, both available from KCI of San Antonio, Texas.

The fourth layer 220 may include either or both of hydrophobic and hydrophilic materials. In an example in which the fourth layer 220 may be hydrophilic, the fourth layer 220 may also wick fluid away from a tissue site, while continuing to distribute negative pressure to the tissue site. The wicking properties of the fourth layer 220 may draw fluid away from a tissue site by capillary flow or other wicking mechanisms. An example of a hydrophilic foam is a polyvinyl alcohol, open-cell foam such as V.A.C. WHITEFOAM™ Dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

The fourth layer 220 generally has a first planar surface and a second planar surface opposite the first planar surface. The thickness of the fourth layer 220 between the first planar surface and the second planar surface may also vary according to needs of a prescribed therapy. For example, the thickness of the fourth layer 220 may be decreased to relieve stress on other layers and to reduce tension on peripheral tissue. The thickness of the fourth layer 220 can also affect the conformability of the fourth layer 220. In some embodiments, a thickness in a range of about 5 millimeters to 10 millimeters may be suitable.

Individual components of the tissue interface 120, and more generally the dressing 110, may be bonded or otherwise secured to one another with a solvent or non-solvent adhesive, or with thermal welding, for example, without adversely affecting fluid management. Further, the dressing 110 may be provided with different combinations of the individual layers and components. For example, the tissue interface 120 may be provided as a standalone product for applying to a tissue site. In some further embodiments, individual layers of the tissue interface 120 and the dressing 110 may be omitted.

In the example of FIG. 2, the dressing 110 may further include an attachment device, such as an adhesive 260. The adhesive 260 may be, for example, a medically-acceptable, pressure-sensitive adhesive that extends about a periphery, a portion, or the entire cover 125. In some embodiments, for example, the adhesive 260 may be an acrylic adhesive having a coating weight between 25-65 grams per square meter (g.s.m.). Thicker adhesives, or combinations of adhesives, may be applied in some embodiments to improve the seal and reduce leaks. The adhesive 260 may be a layer having substantially the same shape as the periphery 225 of the first layer 205. In some embodiments, such a layer of the adhesive 260 may be continuous or discontinuous. Discontinuities in the adhesive 260 may be provided by apertures or holes (not shown) in the adhesive 260. The apertures or holes in the adhesive 260 may be formed after application of the adhesive 260 or by coating the adhesive 260 in patterns on a carrier layer, such as, for example, a side of the cover 125. Apertures or holes in the adhesive 260 may also be sized to enhance the MVTR of the dressing 110 in some example embodiments.

The cover 125, the first layer 205, the second layer 210, the third layer 215, and the fourth layer 220, or various combinations may be assembled before application or in situ. For example, the first layer 205, the second layer 210, the third layer 215, and the fourth layer 220 of the tissue interface 120 may be positioned in a stacked arrangement, with the cover 125 having the adhesive 260 positioned on its underside placed over the layers of the tissue interface 120 to hold the tissue interface 120 in place over the tissue site. Thus, within the dressing 110, the individual layers of the tissue interface 120, such as the fourth layer 220, may be allowed some degree of movement within the dressing 110. In other instances, the cover 125 may be laminated to portions of the fourth layer 220 and the first layer 205, and the third layer 215 may be laminated to the first layer 205 and to the fourth layer 220 opposite the cover 125 in some embodiments. The second layer 210 may also be coupled to the first layer 205 opposite the third layer 215, and may form a substantial portion of the first side 202, or tissue-facing surface, of the tissue interface 120, in some embodiments. In some embodiments, one or more layers of the tissue interface 120 may be coextensive. For example, the fourth layer 220 may be coextensive with the third layer 215, as illustrated in the embodiment of FIG. 2. In some embodiments, the dressing 110 may be provided as a single, composite dressing. For example, the first layer 205 may be coupled to the cover 125 to enclose the third layer 215 and the fourth layer 220, wherein the second layer 210 is coupled to a tissue-facing side of the first layer 205.

As illustrated in the example of FIG. 2, in some embodiments, a release liner 265 may be attached to or positioned adjacent to the second layer 210 and portions of the first layer 205 on the first side 202 of the tissue interface 120 to protect the adhesive 260 prior to use. The release liner 265 may also provide stiffness to assist with, for example, deployment of the dressing 110. The release liner 265 may be, for example, a casting paper, a film, or polyethylene. Further, in some embodiments, the release liner 265 may be a polyester material such as polyethylene terephthalate (PET), or similar polar semi-crystalline polymer. The use of a polar semi-crystalline polymer for the release liner 265 may substantially preclude wrinkling or other deformation of the dressing 110. For example, the polar semi-crystalline polymer may be highly orientated and resistant to softening, swelling, or other deformation that may occur when brought into contact with components of the dressing 110, or when subjected to temperature or environmental variations, or sterilization. In some embodiments, the release liner 265 may have a surface texture that may be imprinted on an adjacent layer, such as the first layer 205. Further, a release agent may be disposed on a side of the release liner 265 that is configured to contact the first layer 205. For example, the release agent may be a silicone coating and may have a release factor suitable to facilitate removal of the release liner 265 by hand and without damaging or deforming the dressing 110. In some embodiments, the release agent may be a fluorocarbon or a fluorosilicone, for example. In other embodiments, the release liner 265 may be uncoated or otherwise used without a release agent.

FIG. 2 also illustrates one example of a fluid conductor 270 and a dressing interface 275. As shown in the example of FIG. 2, the fluid conductor 270 may be a flexible tube, which can be fluidly coupled on one end to the dressing interface 275. The dressing interface 275 may be an elbow connector, as shown in the example of FIG. 2, which can be placed over an aperture 280 in the cover 125 to provide a fluid path between the fluid conductor 270 and the tissue interface 120. In some embodiments, the fluid conductor 270 may also include a fluid delivery conduit for use with instillation therapy. Further, in some embodiments, the dressing interface 275 may include multiple fluid conduits, such as a conduit for communicating negative pressure and a fluid delivery conduit. For example, the dressing interface 275 may be a V.A.C. VERAT.R.A.C.™ Pad.

In some embodiments of the dressing 110, one or more components of the dressing 110 may additionally be treated with an antimicrobial agent. For example, the first layer 205, the second layer 210, the third layer 215, and/or the fourth layer 220 may be coated with an antimicrobial agent. In some embodiments, the third layer 215 may comprise a polymer coated or mixed with an antimicrobial agent. In other examples, the cover 125, the fluid conductor 270, the dressing interface 275, or other portion of the dressing 110 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

In use, the release liner 265 (if included) may be removed to expose the second layer 210 and portions of the first layer 205, which may be placed within, over, on, or otherwise proximate to a tissue site, particularly a surface tissue site and adjacent epidermis. The first layer 205, the second layer 210, and the third layer 215 may be interposed between the fourth layer 220 and the tissue site, which can substantially reduce or eliminate adverse interaction with the fourth layer 220. For example, the first layer 205, with the second layer 210 coupled to a tissue-facing surface of the first layer 205 on the first side 202 of the tissue interface 120, may be placed over a surface wound (including edges of the wound) and undamaged epidermis to prevent direct contact with the fourth layer 220. Treatment of a surface wound or placement of the dressing 110 on a surface wound includes placing the dressing 110 immediately adjacent to the surface of the body or extending over at least a portion of the surface of the body. Treatment of a surface wound does not tend to include placing the dressing 110 wholly within the body or wholly under the surface of the body, such as placing a dressing within an abdominal cavity. In some applications, the second layer 210 may be positioned adjacent to the treatment aperture 230 of the first layer 205, such that the second layer 210 may be positioned adjacent to, proximate to, or covering a tissue site between the treatment aperture 230 of the first layer 205 and the tissue site. In some applications, at least some portion of the third layer 215 and the fluid restrictions 255 may be exposed to a tissue site through the first layer 205 and voids or openings in the second layer 210. The periphery 225 of the first layer 205 may be positioned adjacent to or proximate to tissue around or surrounding the tissue site. The first layer 205 may be sufficiently tacky to hold the dressing 110 in position, while also allowing the dressing 110 to be removed or re-positioned without trauma to the tissue site.

Removing the release liner 265 can also expose the adhesive 260, and the cover 125 may be attached to an attachment surface. For example, the cover 125 may be attached to epidermis peripheral to a tissue site, around the fourth layer 220 and the third layer 215. The adhesive 260 may be in fluid communication with an attachment surface through the apertures 235 in at least the periphery 225 of the first layer 205 in some embodiments. The adhesive 260 may also be in fluid communication with the edges 245 through the apertures 235 exposed at the edges 245. The second layer 210 may be positioned against the tissue site and may be surrounded by portions of the periphery 225 of the first layer 205 and portions of the adhesive 260 passing through the apertures 235 in the periphery 225 of the first layer 205. In some embodiments, due to the presence of voids, apertures, or openings in the second layer 210, portions of the adhesive 260 may pass through apertures 235 of the first layer 205 as well as through openings in the second layer 210 to come into contact with and adhere to the attachment surface surrounding the tissue site. Thus, to the extent that the second layer 210 may overlap with the periphery 225 of the first layer 205, portions of the tissue site or areas surrounding the tissue site that may be adjacent to the periphery 225 of the first layer 205 may be in contact with portions of each of the first layer 205, the enzyme-neutralizing material of the second layer 210, and adhesive 260.

Once the dressing 110 is in the desired position, the adhesive 260 may be pressed through the apertures 235 to bond the dressing 110 to the attachment surface, such as the epidermis surrounding the tissue site. The apertures 235 at the edges 245 may permit the adhesive 260 to flow around the edges 245 for enhancing the adhesion of the edges 245 to the attachment surface. In some embodiments, the bond strength of the adhesive 260 may vary in different locations of the dressing 110.

The geometry and dimensions of the tissue interface 120, the cover 125, or both may vary to suit a particular application or anatomy. For example, the geometry or dimensions of the tissue interface 120 and the cover 125 may be adapted to provide an effective and reliable seal against challenging anatomical surfaces, such as an elbow or heel, at and around a tissue site. Additionally or alternatively, the dimensions may be modified to increase the surface area for the first layer 205 to enhance the movement and proliferation of epithelial cells at a tissue site and reduce the likelihood of granulation tissue in-growth.

Thus, the dressing 110 in the example of FIG. 2 can provide a sealed therapeutic environment proximate to a tissue site, substantially isolated from the external environment, and the negative-pressure source 105 can reduce the pressure in the sealed therapeutic environment. Further, the dressing 110 may permit re-application or re-positioning, to correct air leaks caused by creases and other discontinuities in the dressing 110, for example. The ability to rectify leaks may increase the efficacy of the therapy and reduce power consumption in some embodiments.

If not already configured, the dressing interface 275 may be disposed over the aperture 280 and attached to the cover 125. The fluid conductor 270 may be fluidly coupled to the dressing interface 275 and to the negative-pressure source 105.

In some applications, a filler may also be disposed between a tissue site and the tissue interface 120, such as between the tissue site and the second layer 210 of the tissue interface 120. For example, if the tissue site is a surface wound, a wound filler may be applied interior to the peri-wound, and portions of the second layer 210 and/or the first layer 205 may be disposed over the peri-wound and the wound filler. In some embodiments, the filler may be a manifold, such as an open-cell foam. The filler may comprise or consist essentially of the same material as the fourth layer 220 in some embodiments.

Negative pressure applied through the tissue interface 120 can create a negative pressure differential across the fluid restrictions 255 in the third layer 215, which can open or expand the fluid restrictions 255 from their resting state. For example, in some embodiments in which the fluid restrictions 255 may comprise substantially closed fenestrations through the third layer 215, a pressure gradient across the fenestrations can strain the adjacent material of the third layer 215 and increase the dimensions of the fenestrations to allow liquid movement through them, similar to the operation of a duckbill valve. Opening the fluid restrictions 255 can allow exudate and other liquid movement through the fluid restrictions 255 and into the fourth layer 220 and the container 115. Changes in pressure can also cause the fourth layer 220 to expand and contract, and the third layer 215 as well as portions of the first layer 205 may protect the epidermis from irritation caused by movement of the fourth layer 220. The third layer 215, the first layer 205, as well as the second layer 210, can also substantially reduce or prevent exposure of tissue to the fourth layer 220, which can inhibit growth of tissue into the fourth layer 220.

If the negative-pressure source 105 is removed or turned-off, the pressure differential across the fluid restrictions 255 can dissipate, allowing the fluid restrictions 255 to move to their resting state and prevent or reduce the rate at which exudate or other liquid can return to the tissue site through the third layer 215. The second layer 210 may provide an additional means to protect the tissue site from prolonged contact with exudates containing proteolytic enzymes, should the exudate pass back through the fluid restrictions 255 of the third layer 215, or otherwise bypass the third layer 215 and pass through the first layer 205 to be in contact with the tissue site. Such circumstances may have a higher chance of occurring in applications of highly-exuding wounds or in the instance of a failure with the application, configuration, or function of the dressing 110 and/or negative-pressure source 105 of the therapy system 100.

Figure 3:
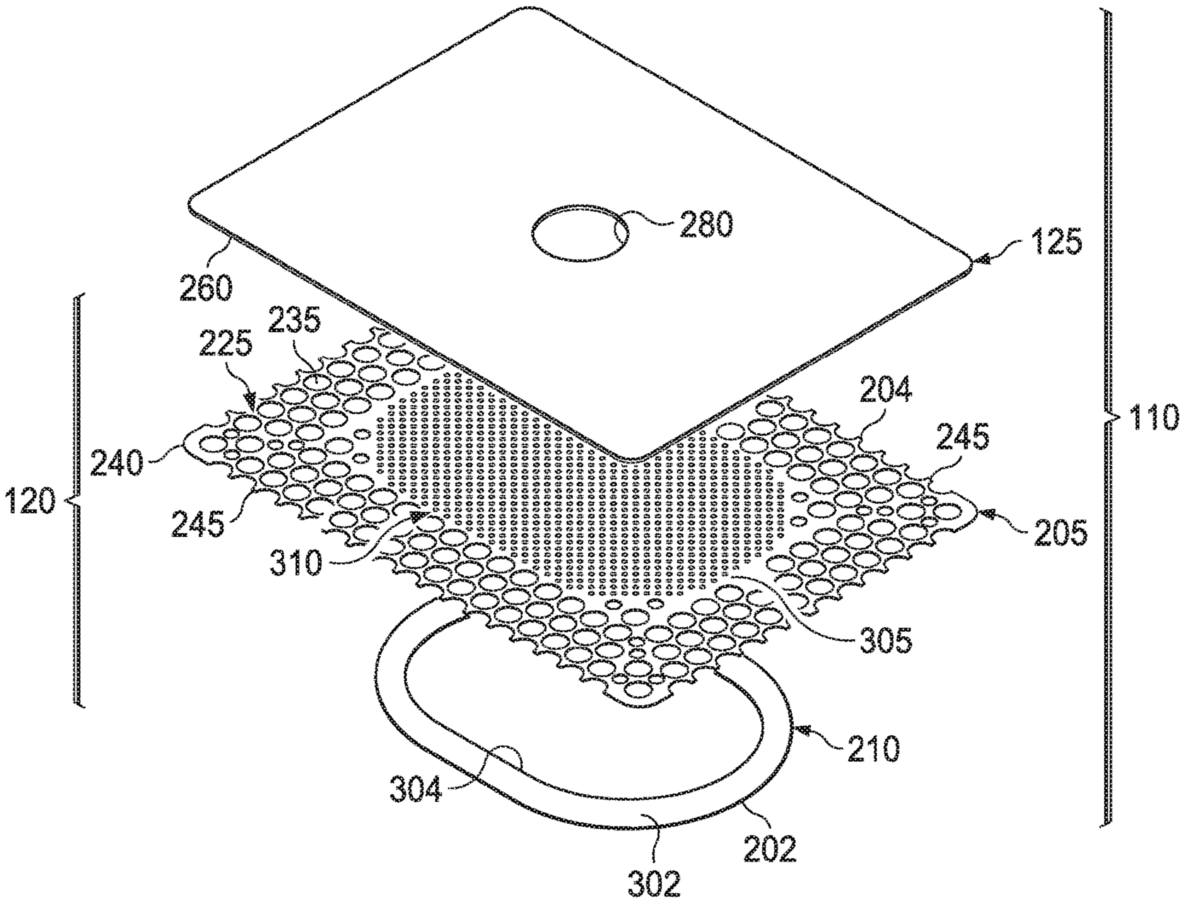
FIG. 3 is an assembly view of another example of a dressing illustrating additional details that may be associated with some example embodiments of the therapy system of FIG. 1.

FIG. 3 is an assembly view of another example of the dressing 110, illustrating additional details that may be associated with some embodiments. Among other things, FIG. 3 illustrates another example of the second layer 210. While some of the components of the dressing 110 of FIG. 3 may be the same as or similar to those of the dressing 110 of FIG. 2, the arrangement and/or order of the layers of the dressing 110 of FIG. 3 may be different. While the illustrative embodiment of the dressing 110 shown in FIG. 3 omits some of the layers of the dressing 110 of FIG. 2, alternative embodiments may include one or more of the omitted layers in combination with the layers of the embodiment shown in FIG. 3. The second layer 210 of FIG. 3 may comprise one or more enzyme-modulating or enzyme-neutralizing materials as described with respect to the second layer 210 of FIG. 2 and may be in the form of a ring-shaped layer positioned adjacent to the first layer 205 on the first side 202 of the tissue interface 120. For example, the second layer 210 may be in the form of a ring-shaped layer having an outer structural portion 302 comprising the one or more enzyme-neutralizing materials, and an opening 304. In some alternative embodiments, the second layer 210 may have a different shape, such as a square, circular, or rectangular shape. In addition to or instead of being included as a separate layer, the material of the second layer 210 may be printed or pattern-coated on a surface of the first layer 205 on the first side 202 of the tissue interface 120.

In the embodiment depicted in FIG. 3, the first layer 205 may have an interior border 305 around an interior portion having a plurality of treatment apertures 310. The interior border 305 may be disposed between the plurality of treatment apertures 310 and the periphery 225. The interior border 305 may be substantially free of apertures, as illustrated in the example of FIG. 3. The interior portion comprising the plurality of treatment apertures 310 may be symmetrical and centrally disposed in the first layer 205.

In some embodiments, the diameter of the apertures 235 in the periphery 225 of the first layer 205 may be larger than the diameter of the treatment apertures 310 in the interior portion of the first layer 205. For example, in some embodiments, the apertures 235 disposed in the periphery 225 may have a diameter between about 9.8 millimeters to about 10.2 millimeters, while the apertures 235 disposed in the corners 240 may have a diameter between about 7.75 millimeters to about 8.75 millimeters. In some embodiments, the treatment apertures 310 disposed in the interior portion of the first layer 205 may have a diameter between about 1.8 millimeters to about 2.2 millimeters.

As shown in FIG. 3, in some embodiments, the second layer 210 may have the shape of an oval ring that may align with a portion of the first layer 205. The opening 304 may be fluidly coupled to one or more of the treatment apertures 310. For example, the opening 304 may be aligned with one or more of the treatment apertures 310, or the opening 304 may substantially surround the treatment apertures 310. The second layer 210 may substantially align with the interior border 305 of the first layer 205 in some example embodiments. In some examples, the opening 304 may have a width of about 3 centimeters to about 35 centimeters. A width of about 12 centimeters to about 24 centimeters may be suitable for some embodiments. The second layer 210 may provide a form of barrier or border on the first side 202 of the tissue interface 120, such that the proteolytic enzymes in fluids exuding from the tissue site may come into contact with a portion of the enzyme-neutralizing material of the second layer 210 before traveling outwards away from the center of the tissue site and the tissue interface 120 towards the peri-wound area.

Figure 4:
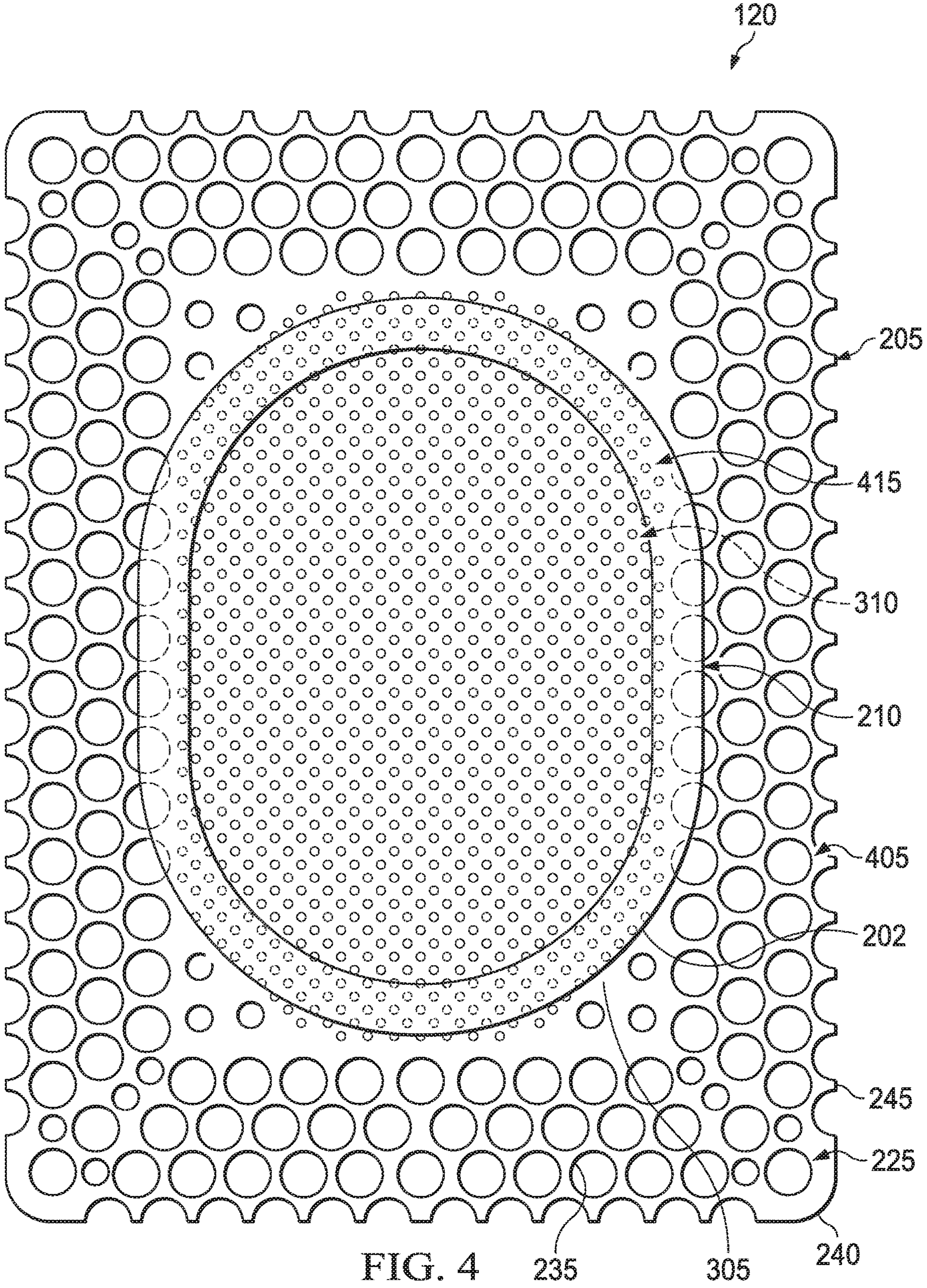
FIG. 4 is a schematic view of an example configuration of an example first layer of a dressing overlaid on an example second layer of a dressing, illustrating additional details that may be associated with some embodiments of the dressing of FIG. 3.

FIG. 4 is a schematic view of the embodiment of the tissue interface 120 of FIG. 3, from the perspective of the first side 202 of the tissue interface 120. As shown in FIG. 4, the second layer 210 may be positioned against a portion of the first layer 205. For example, the first layer 205 may have a first surface 405 that forms at least a portion of the first side 202 of the tissue interface 120. The second layer 210 may also have a first surface 415 that forms at least a portion of the first side 202 of the tissue interface 120. As shown in FIG. 4, the second layer 210 may be positioned against the first layer 205, such that the second layer 210 is in contact with a significant portion of the first surface 405 of the first layer 205.

As also shown in FIG. 4, the second layer 210 may be sized and positioned such that the second layer 210 substantially aligns with the interior border 305 of the first layer 205. The material of the second layer 210 may also align with a portion of the interior portion of the first layer 205 comprising the plurality of treatment apertures 310 and and/or a portion of the periphery 225 of the first layer 205. In some examples, the second layer 210 may obstruct or cover at least portions of some of the apertures 235 of the periphery 225, without interfering with proper adhesion of the dressing 110 to the tissue site. For example, a sufficient amount of adhesive 260 may be able to pass through the remaining apertures 235 of the periphery 225 so as to form a sufficient seal around the tissue site. In some embodiments, the material of the second layer 210 may be printed or coated on the first side 202 of the tissue interface 120 following assembly of the other layers of the dressing 110, such that the second layer 210 is partially applied to a surface of the first layer 205 as well as applied to portions of the adhesive 260 that may be exposed through the apertures 235 in the periphery 225 of the first layer 205.

The second layer 210 may be positioned so as to particularly protect the margins or peri-wound of the tissue site from an abundance of proteolytic enzymes. For example, during the administration of negative-pressure therapy, fluid may be drawn from the tissue site into contact with the first side 202 of the tissue interface 120. While the fluid may typically travel through the plurality of treatment apertures 310 of the first layer 205 and towards the aperture 280 on the cover 125 of the dressing 110, in some cases, at least some fluid may also travel laterally across the surface of the tissue site or the first side 202 of the tissue interface 120 towards the peri-wound area. By positioning the second layer 210 on the first side 202 of the tissue interface 120, fluid traveling towards the peri-wound regions first passes through at least a portion of the second layer 210 before reaching the outer perimeter of the tissue site, or peri-wound. As a result, the second layer 210 may, in effect, serve as an enzyme-neutralizing filter through which fluid from the center portion of the tissue site and dressing 110 must travel before reaching outer portions of the tissue site and/or dressing 110. Such an arrangement may minimize or prevent exposure of the wound margins and/or peri-wound to wound fluids that may contain excess proteolytic enzymes. The second layer 210 may also protect the peri-wound from proteolytic enzymes in wound fluids that could possibly travel back down from other layers of the tissue interface 120 towards the tissue site and possibly outwards towards the peri-wound areas.

Figure 5:
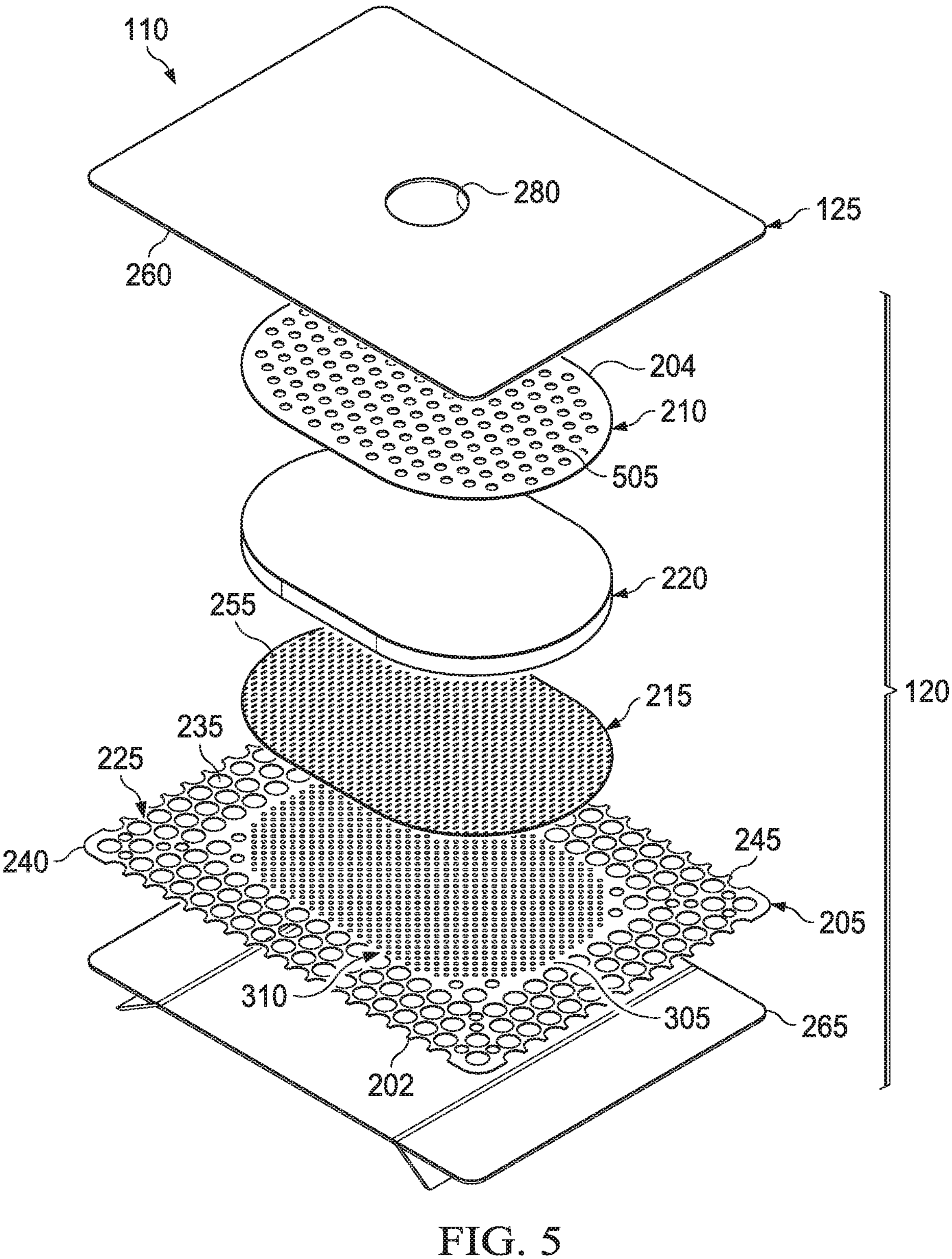
FIG. 5 is an assembly view of another example of a dressing illustrating additional details that may be associated with some example embodiments of the therapy system of FIG. 1.

FIG. 5 is an assembly view of another example of the dressing 110. For example, the individual layers of the tissue interface 120 of FIG. 5 may be arranged or stacked in a different order than the layers of the tissue interface 120 of FIG. 2. More specifically, in some embodiments, the second layer 210 of FIG. 5 may be placed adjacent to the fourth layer 220, or between the fourth layer 220 and the cover 125 of the dressing 110. As shown in FIG. 5, the second layer 210 may have an oval shape similar to other layers of the tissue interface 120, such as the third layer 215 and the fourth layer 220. In other examples, the second layer 210 of FIG. 5 may also have different shapes or configurations, such as a square, circular, or X-shaped configuration. Additionally or alternatively, the second layer 210 of FIG. 5 may comprise a grid-like structure, similar to that of FIG. 2. As illustrated in FIG. 5, in some embodiments, the second layer 210 may include a plurality of apertures or openings, such as perforations 505, for allowing the communication of negative pressure, as well as the transfer of fluids, such as wound fluids, through the second layer 210 and towards the aperture 280 in the cover 125 of the dressing 110. For example, the perforations 505 may each have a diameter of between 1 mm and 10 mm, and in some embodiments may have a circular shape with a diameter of between 1 mm and 5 mm. In some additional embodiments, the second layer 210 may include a plurality of openings in the form of slots, with each of the slots having a length between 1 mm and 5 mm and a width between 0.5 mm and 2 mm.

In some embodiments, the second layer 210 may include an enzyme-neutralizing material that may be varied spatially across the second layer 210. In some embodiments, the enzyme-neutralizing material may be disposed within or dispersed across the second layer 210 according to a gradient. For example, the second layer 210 may include a lower concentration of enzyme-neutralizing material, such as one or more of a sacrificial substrate, enzyme deactivator, or enzyme sequestrator, in a central portion of the second layer 210, with the concentration of enzyme-neutralizing material increasing with increasing distance from the center of the second layer 210 towards the edges or perimeter of the second layer 210. In some embodiments, the enzyme-neutralizing material may have a circular concentration gradient with a higher concentration in a perimeter than at a center portion. In some embodiments, a concentration of about 100-450 $mg/cm^2$ may be suitable for a perimeter portion, and a concentration of about 1-75 $mg/cm^2$ may be suitable for a center portion. Including a higher concentration of the enzyme-neutralizing material in the peripheral portions of the second layer 210 that may be in closer proximity with the peri-wound area may ensure that the peri-wound is not exposed to excessive levels of proteolytic enzymes that could lead to maceration of the peri-wound tissue. Including a higher concentration of the enzyme neutralizing material in the outer, or peripheral, portions of the second layer 210 may also enhance the antimicrobial capabilities of the second layer 210 to ensure that wound fluids that may travel away from the center portion of the tissue interface 120, and potentially towards the wound margins, may be treated by the second layer 210.

Still referring primarily to FIG. 5, the dressing 110 may further include features designed to ensure structural stability of the dressing 110 over time as some of the enzyme-neutralizing material of the second layer 210 may be degraded due to prolonged contact with wound fluids containing proteolytic enzymes. Although not specifically shown in FIG. 5, in some instances, additional polymeric welds may be included in the dressing 110 that pass through the second layer 210 and bond two or more layers surrounding the second layer 210 to each other to prevent or minimize movement between or separation of layers of the dressing 110 from each other. For example, depending on the particular arrangement of layers in a particular embodiment of the dressing 110, polymeric welds may be created that completely pass through the second layer 210 of the dressing 110, or any other layer comprising the enzyme-neutralizing material in other example embodiments, and bond a top adhesive layer, such as the cover 125 with a base or sealing layer, such as the first layer 205.

The tissue interface 120 and dressing 110 may be provided with different combinations of the individual layers, as well as different combinations of the materials within one or more of the layers. In some embodiments, instead of or in addition to being applied in a separate layer of the tissue interface 120, enzyme-neutralizing material may be applied on one of the other layers of the tissue interface 120. For example, various layers of the tissue interface 120 may be assembled, and then the enzyme-neutralizing material may be printed or coated on a surface of the first layer 205 on the first side 202 of the tissue interface 120. Additionally, in some additional embodiments, materials for reducing or neutralizing proteolytic activity in wound fluids may be included in additional or alternative portions of the tissue interface 120, as well as more generally the dressing 110. For example, the materials for reducing proteolytic activity may be combined or integrated with the material of one or more of the other layers of the tissue interface 120. In an example embodiment, one or more enzyme-neutralizing materials may be compounded with a post-cured silicone adhesive formulation of the first layer 205, in addition to or instead of being included as a separate enzyme-neutralizing layer.

In some further embodiments, additional materials for reducing or neutralizing proteolytic enzyme activity may be added to one or more layers of the tissue interface 120. For example, a synthetic or naturally-occurring protease inhibitor in the form of a protein, peptides, or small molecules may be added to an enzyme-neutralizing layer, such as the second layer 210, for providing a further means for neutralizing proteolytic enzymes. For example, protease inhibitors may include a tissue inhibitor of metalloproteinases (TIMPs), thrombospondin-1, thrombospondin-2, elastase inhibitor 2, alpha 1 antitrypsin, pepstatin A, aprotinin, EDTA, leupeptin, among others. Some examples of naturally-occurring protease inhibitors include, but are not limited to, thionins commonly found in potato tubers and known to also contain antimicrobial compounds, green tea catechin, blue-green algae, and members of the families of Leguminosae Malvaceae, Rutaceae, Graminae, and Moringaceae.

The systems, apparatuses, and methods described herein may provide significant advantages. For example, the dressing 110 may be a fully-integrated negative-pressure therapy dressing that can be applied to a tissue site (including on the peri-wound) for long-term wear to promote granulation, while offering benefits of protecting the periphery of the tissue site from maceration. For example, the inclusion in the tissue interface 120 and/or dressing 110 of one or more substrates for neutralizing proteolytic enzymes may protect the tissue site, including the peri-wound, by reducing or preventing potential detrimental effects due to increased levels of inflammatory cells and proteases in wound fluids. The one or more enzyme-neutralizing substrates may prevent excessive levels of enzymatic proteases from being in contact with the tissue site, while still allowing the proteases to have their beneficial effects for advancing normal wound healing. For example, normal levels of proteases may help with degrading denatured extracellular matrix (ECM), which may allow the functional matrix to be exposed in healing tissue. Including the one or more enzyme-neutralizing substrates may prevent disruption in the wound healing system due to elevated numbers of proteases and a resulting distortion in the ratio of the proteases to their inhibitors, which may otherwise lead to degradation of ECM that forms during the wound healing process and corresponding inhibited wound healing.

Such benefits may be particularly realized in applications of the dressing 110 to tissue sites producing higher amounts of wound exudates, such as chronic wounds where managing the wound environment and moisture balance at the tissue site may be particularly challenging. When applied to chronic wounds where the level of proteolytic enzymes present in wound fluids at a tissue site may be increased, the inclusion of one or more enzyme-neutralizing materials in a layer of the dressing 110 may be particularly advantageous for achieving longer wear times. For example, longer wear times, such as up to seven days, may be achieved, while minimizing risks of maceration to the peri-wound area that may otherwise exist due to potential prolonged contact with wound fluids containing proteolytic enzymes. Furthermore, since the dressing 110 may also cover the peri-wound, providing the enzyme-neutralizing materials in a layer between the other layers of the tissue interface 120 and the tissue site, such as on a tissue-facing surface of the tissue interface 120, may offer particular protection of the peri-wound by neutralizing proteolytic enzymes found in wound exudates present at the surface of the tissue site. Thus, in many instances, the proteolytic enzymes may be neutralized before coming into contact with the peri-wound area, thereby preventing prolonged exposure of the wound margins, such as the peri-wound, to wound fluids and the associated proteases and inflammatory cells. Additionally, the dressing 110 may provide macro-strains to the edges of a tissue site, such as wound edges, while substantially reducing or preventing maceration of the surrounding peri-wound area.

Including the enzyme-neutralizing material in the dressing 110 may additionally offer antimicrobial benefits, which may also extend the usable life of the dressing 110. By providing an antimicrobial effect, the enzyme-neutralization material may significantly reduce infection risks that may be associated with prolonged wear time of dressings, particularly when applied to infected or highly exuding wounds. Thus, the dressing 110 may offer an extended-wear solution capable of preventing maceration and potential build-up of microbial matter, while maintaining a good seal around the tissue site as well as unobstructed pathways for negative-pressure therapy.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may also be combined or eliminated in various configurations for purposes of sale, manufacture, assembly, or use. For example, in some configurations the dressing 110 may be separated from other components for manufacture or sale. In other example configurations, the dressing 110 or the tissue interface 120 may also be manufactured, configured, assembled, or sold as a kit, independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, comprising:

a first layer comprising a hydrophobic gel having at least one treatment aperture and a periphery surrounding the treatment aperture;

a second layer covering at least a portion of the periphery of the first layer on a side of the first layer configured to face toward the tissue site, the second layer comprising a material adapted to neutralize proteolytic enzymes;

a third layer adjacent to the first layer, the third layer comprising a non-porous film that includes a plurality of perforations;

a fourth layer positioned in contact with the third layer and on an opposite side of the third layer from the first layer, the fourth layer comprising a manifold; and a fifth layer adjacent to the fourth layer opposite the third layer, the fifth layer comprising a polymer drape.

2. The dressing of claim 1, wherein the material adapted to neutralize proteolytic enzymes comprises a sacrificial substrate.

3. The dressing of claim 1, wherein the material adapted to neutralize proteolytic enzymes comprises one or both of an enzyme sequestrator or an enzyme deactivator.

4. The dressing of claim 1, wherein the second layer comprises a biologically-derived polymer.

5. The dressing of claim 1, wherein the second layer comprises one or a combination of collagen, gelatin, collagen-like proteins, collagen-like peptides, cellulose, or cellulose derivative.

6. The dressing of claim 1, wherein the second layer comprises collagen and oxidized regenerated cellulose.

7. The dressing of claim 1, wherein the second layer forms a ring.

8. The dressing of claim 1, wherein the second layer comprises an opening aligned with the treatment aperture.

9. The dressing of claim 1, wherein the second layer comprises an opening having a width in a range of about 3 centimeters to about 35 centimeters.

10. The dressing of claim 1, wherein the second layer has a thickness of between 5 micrometers and 500 micrometers.

11. The dressing of claim 1, wherein the second layer comprises approximately 20-80% collagen and 80-20% ORC by weight.

12. The dressing of claim 1, wherein the second layer comprises approximately 55% collagen and 45% ORC by weight.

13. The dressing of claim 1, wherein the material adapted to neutralize proteolytic enzymes is present at a higher concentration in a perimeter portion than at a center portion of the second layer.

14. The dressing of claim 1, wherein the material adapted to neutralize proteolytic enzymes is present in a concentration having a circular gradient increasing from a center portion of the second layer to a perimeter of the second layer.

15. The dressing of claim 1, wherein the perforations are defined by cut or removed portions of the non-porous film.

16. A system for treating a tissue site, comprising:

the dressing of claim 1; and a negative-pressure source adapted to be fluidly coupled to the dressing.

* * * * *